United States Patent
Maccagnan et al.

(10) Patent No.: US 11,806,442 B2
(45) Date of Patent: Nov. 7, 2023

(54) SYSTEM AND METHODS FOR HARVESTING AND PROCESSING PERIOSTEUM FIBERS

(71) Applicant: Allosource, Centennial, CO (US)

(72) Inventors: Megan Maccagnan, Golden, CO (US); Cameron Mattson, Morrison, CO (US); Cole Watkins, Fort Collins, CO (US); Adrian C. Samaniego, Centennial, CO (US); William Maslanik, Littleton, CO (US)

(73) Assignee: Allosource, Centennial, CO (US)

( * ) Notice: Subject to any disclaimer, the term of this patent is extended or adjusted under 35 U.S.C. 154(b) by 629 days.

(21) Appl. No.: 16/571,632

(22) Filed: Sep. 16, 2019

(65) Prior Publication Data

US 2020/0086001 A1  Mar. 19, 2020

Related U.S. Application Data (60) Provisional application No. 62/732,210, filed on Sep. 17, 2018.

(51) Int. Cl.
*A61L 27/36* (2006.01)
*C12N 5/071* (2010.01)
*A61B 17/16* (2006.01)

(52) U.S. Cl.
CPC ....... *A61L 27/3608* (2013.01); *A61L 27/3687* (2013.01); *A61L 27/3691* (2013.01); *C12N 5/0697* (2013.01); *A61B 17/1635* (2013.01); *A61L 2430/02* (2013.01); *A61L 2430/38* (2013.01)

(58) Field of Classification Search
CPC .................................................. A61L 27/3608
See application file for complete search history.

(56) References Cited

U.S. PATENT DOCUMENTS

| | | | | |
|---|---|---|---|---|
| 5,970,837 A * | 10/1999 | Arterburn | | D01G 1/04 83/563 |
| 2003/0014124 A1* | 1/2003 | Wolfinbarger, Jr. | | A61L 27/3691 8/94.11 |
| 2007/0078522 A2* | 4/2007 | Griffey | | A61K 47/42 435/378 |
| 2009/0226523 A1* | 9/2009 | Behnam | | A61P 19/08 424/549 |
| 2015/0297793 A1* | 10/2015 | McKay | | A61L 27/3683 424/529 |

OTHER PUBLICATIONS

Abler et al., O'Brien Center For Benign Urologic Research, UW-Madison-UMASS Boston, Tissue embedding in paraffin for sectioning, pp. 1-3, retrieved from the internet: https://niddkcairibu.urology.wisc.edu/wp-content/uploads/sites/1064/2019/08/Tissue_embedding_protocol.pdf (Year: 2015).*
Chen et al., Acta Biomaterialia 19 (2015) 46-55 (Year: 2015).*
Smith et al., Journal of Tissue Engineering and Regenerative Medicine, 2015; 9: 595-604 (Year: 2015).*
Mophorn Wood Lathe, Ubuy, Mophorn Wood Lathe, 5 pages, retrieved from the internet Apr. 14, 2022:https://www.ubuy.co.id/en/product/BRR1RW4-mophorn-wood-lathe-10-x-18-inch-benchtop-heavy-duty-wood-lathe-5-speed-mini-wood-lathe-370w-power-m (Year: 2022).*

* cited by examiner

*Primary Examiner* — Allison M Fox
*Assistant Examiner* — Jennifer S Spence
(74) *Attorney, Agent, or Firm* — James A. Sheridan; Sheridan Law, LLC (57) ABSTRACT

Periosteum harvesting and processing systems and methods enable rapid, efficient, and repeatable harvesting of periosteum tissue from human long bones and processing of the tissue into individual fibers for use in strengthening surgical allograft products. One harvesting and processing method involves providing a human long bone, securing the long bone between two rotating live centers, scraping, using one of a plurality of harvesting tools selected from a harvesting and processing kit, periosteum tissue from the long bone, executing a first wash cycle comprising a hydrogen peroxide wash, executing a second wash cycle comprising an isopropyl alcohol wash, executing a third wash cycle comprising a phosphate buffered saline wash, compressing the periosteum tissue to remove excess fluid, cryofracturing the tissue until a desired fiber size is achieved, and separating the periosteum tissue into individual periosteum fibers having the desired fiber size. Other embodiments are also disclosed.

11 Claims, 10 Drawing Sheets

SYSTEM AND METHODS FOR HARVESTING AND PROCESSING PERIOSTEUM FIBERS

REFERENCE TO PRIOR PATENT APPLICATION

This application claims the benefit under 35 U.S.C. 119(e) of U.S. Provisional Patent Application No. 62/732,210, filed Sep. 17, 2018 by Megan Maccagnan, Cameron Mattson, Cole Watkins, Adrian C. Samaniego, and William Maslanik for "SYSTEM AND METHODS FOR HARVESTING AND PROCESSING PERIOSTEUM FIBERS," all of which patent application is hereby incorporated herein by reference.

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from cadaveric donor-derived, living-related, or living-unrelated donors and can help patients regain mobility, restore function, enjoy a better quality of life, and even save lives in the case of cardiovascular tissue or skin.

Figure 1:
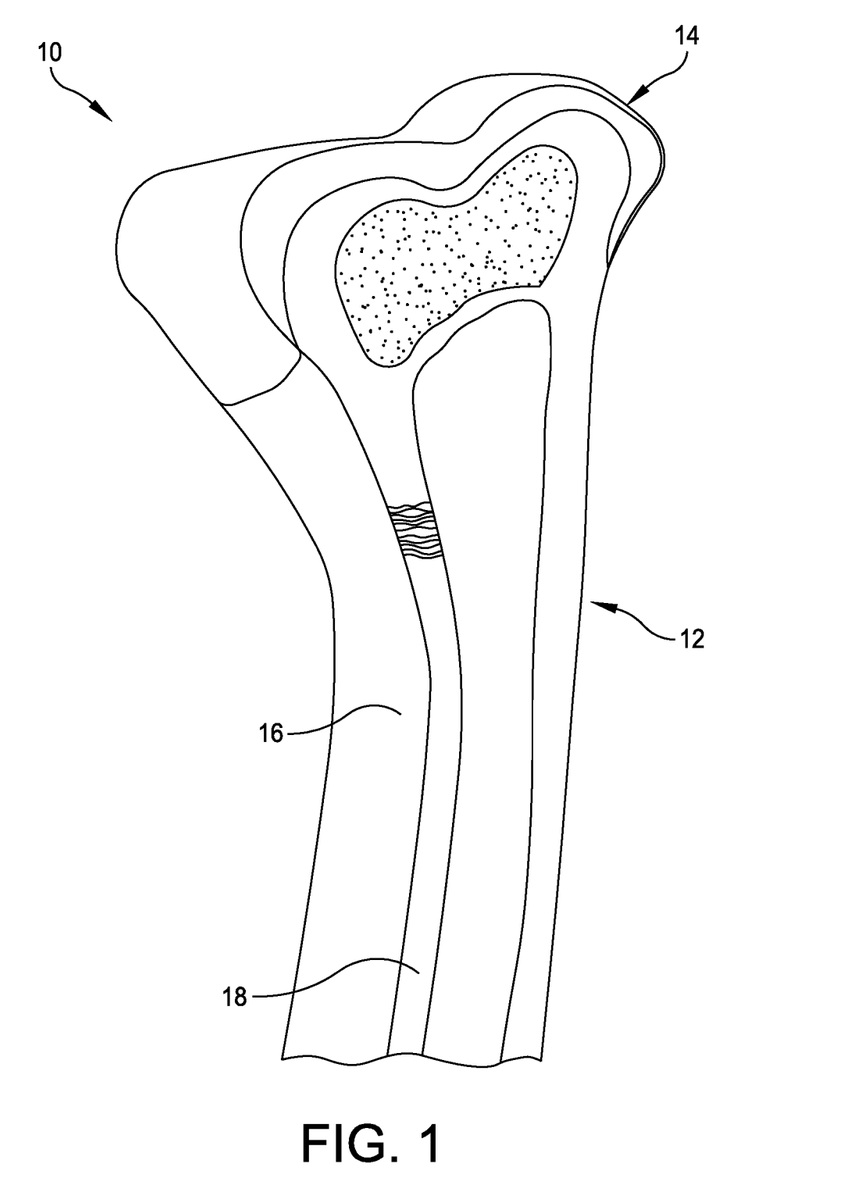
FIG. 1 illustrates a partial cross-sectional view of a human long bone, including a layer of periosteum tissue bordering the cortical bone.

FIG. 1 illustrates a cross-sectional, partial view of a human long bone 10 having a diaphysis (shaft) 12 extending between epiphyses (ends) 14. A periosteum 16 provides a dense layer or membrane of vascular connective tissue that envelops the bone except at the surfaces of the joints. The periosteum 16 borders the dense outer surface of the bone, known as cortical bone 18. Fibers of periosteum are oftentimes used to increase material cohesiveness and provide structural integrity to allograft products designed to be surgical grafts, in a manner similar to the use of rebar within concrete structures. For example, periosteum fibers are often incorporated into surgical grafts for promoting graft cohesiveness in spinal fusion procedures.

Currently, no efficient mechanisms or methods exist for the rapid harvesting of periosteum from human long bones or for processing the periosteum into individual fibers that may then be implemented within surgical allografts. Existing tools and methods present time, efficiency, efficacy, and repeatability challenges.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a composition of periosteum fibers for use in strengthening a surgical allograft prepared by a method comprising the following steps: (1) providing a human long bone including a diaphysis extending between two epiphyses and having an outer layer of a periosteum tissue; (2) removing the epiphyses and securing the diaphysis between two rotating live centers; (3) removing, using one of a plurality of harvesting tools selected from a harvesting and processing kit, the periosteum tissue from the diaphysis; (4) executing a first wash cycle comprising washing the periosteum tissue in a hydrogen peroxide solution; (5) executing a second wash cycle comprising washing the periosteum tissue in an isopropyl alcohol solution; (6) executing a third wash cycle comprising washing the periosteum tissue in a phosphate buffered saline (PBS); (7) compressing the periosteum tissue; (8) cryofracturing the periosteum tissue into a quantity of fused periosteum fibers; and (9) separating the quantity of the fused periosteum fibers into a plurality of individual periosteum fibers.

Another embodiment provides a method of harvesting and processing bulk periosteum tissue. The method may include the following steps: (1) removing, using one or more harvesting tools, a quantity of bulk periosteum tissue from an outer surface of a human long bone; (2) first washing the quantity of the bulk periosteum tissue in a volume of hydrogen peroxide; (3) second washing the quantity of the bulk periosteum tissue in a volume of isopropyl alcohol; (4) third washing the quantity of the bulk periosteum tissue in a volume of phosphate buffered saline (PBS); (5) compressing the quantity of the bulk periosteum tissue; (6) cryofracturing the quantity of the bulk periosteum tissue until the quantity of the bulk periosteum tissue comprises a plurality of individual periosteum fibers; and (7) using a fiber separator tool to separate the plurality of the individual periosteum fibers from one another.

Yet another embodiment provides a method for harvesting and processing periosteum tissue, including the following: (1) providing a periosteum harvesting and processing kit comprising a plurality of periosteum harvesting tools configured for removing an outer layer of periosteum tissue from a human long bone, at least one sieve, at least one compression tool, and a periosteum fiber separator; (2) using at least one of the plurality of the periosteum harvesting tools, removing the periosteum tissue from the human long bone; (3) thrice repeating a first hydrogen peroxide wash cycle; (4) first drying the periosteum tissue; (5) twice repeating a second isopropyl alcohol wash cycle; (6) second drying the periosteum tissue; (7) performing a third phosphate buffered saline (PBS) wash cycle; (8) third drying the periosteum tissue; (9) compressing the periosteum tissue using the at least one compression tool; (10) cryofracturing the periosteum tissue into a plurality of fused periosteum fibers; and (11) separating the plurality of the fused periosteum fibers into a plurality of individual periosteum fibers using the periosteum fiber separator.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to efficiently and rapidly harvesting the periosteum 16 from human long bones 10 (FIG. 1) and processing the harvested bulk periosteum tissue 16 into periosteum fibers for subsequent use in supporting and adding structural integrity to other surgical allograft products. In one embodiment, a periosteum harvesting and processing method may involve scraping or otherwise stripping the periosteum tissue 16 from the long bone, followed by a series of periosteum washing, isolation, compression, cryofracturing, and fiber separation steps. A number of tools may be implemented to carry out the periosteum harvesting and processing method. The tools may be incorporated within a periosteum harvesting and processing kit having a selection of instruments such as scalpels, cheese wires, radius card scrapers, and small radius gouges, each configured for scraping the periosteum 16 from the long bone 10. The kit may also include absorbent materials for fluid removal, compression tools, and separation tools specifically configured for separating clumps of processed bulk periosteum tissue into individual periosteum fibers.

Figure 2A:
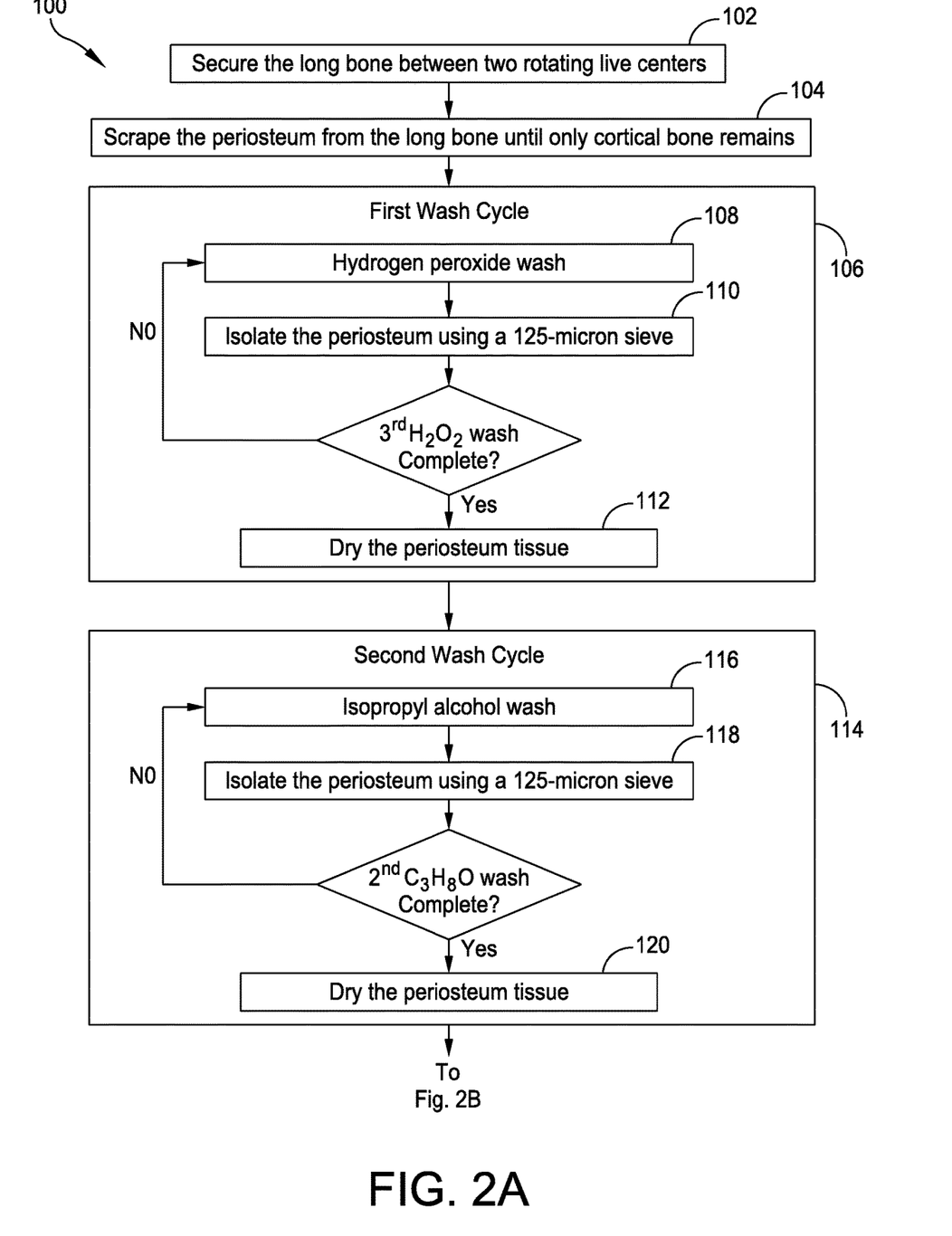
FIGS. 2A-2B provide a flowchart depicting an exemplary method for harvesting periosteum tissue and processing it into individual periosteum fibers.
Figure 2B:
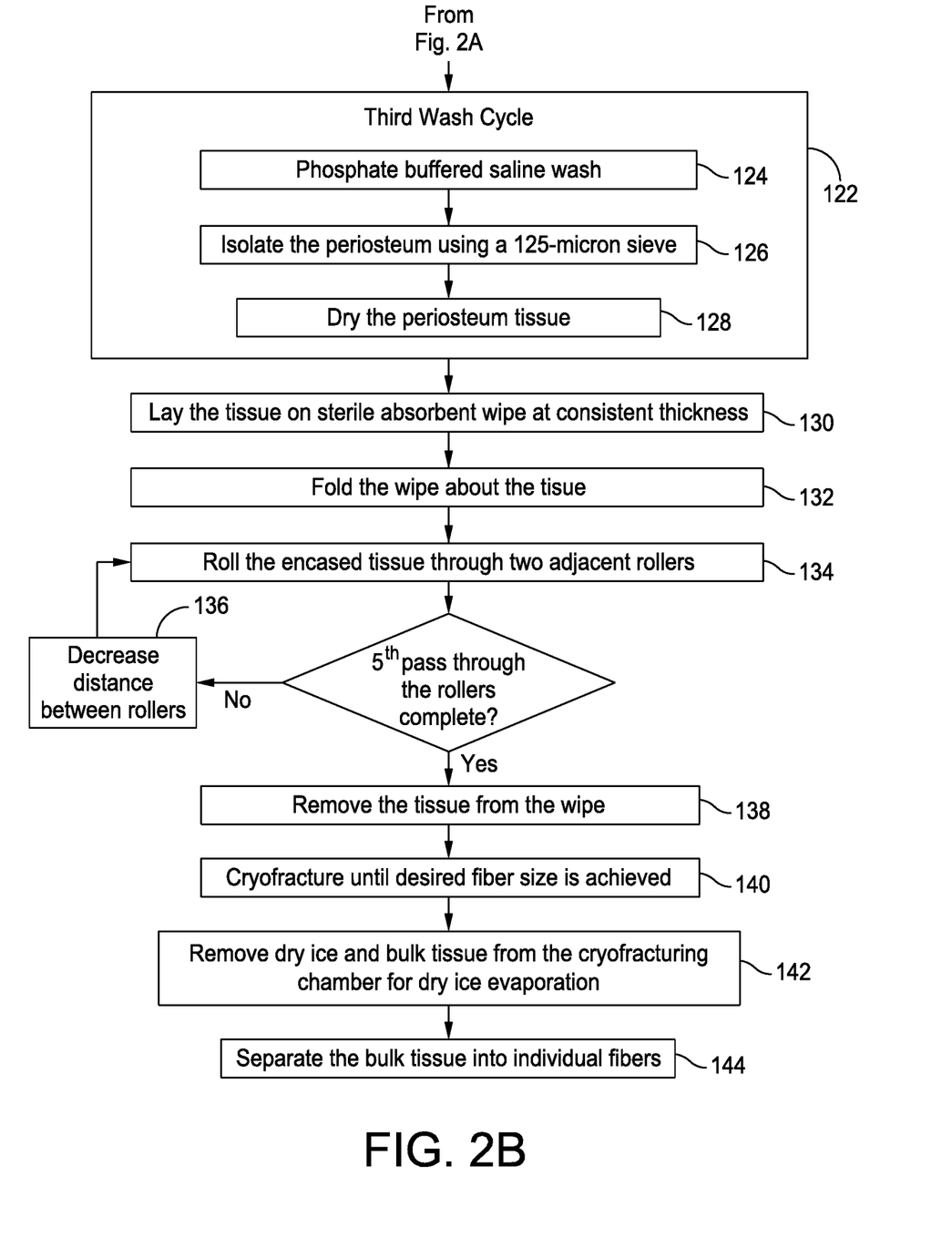
Figure 3:
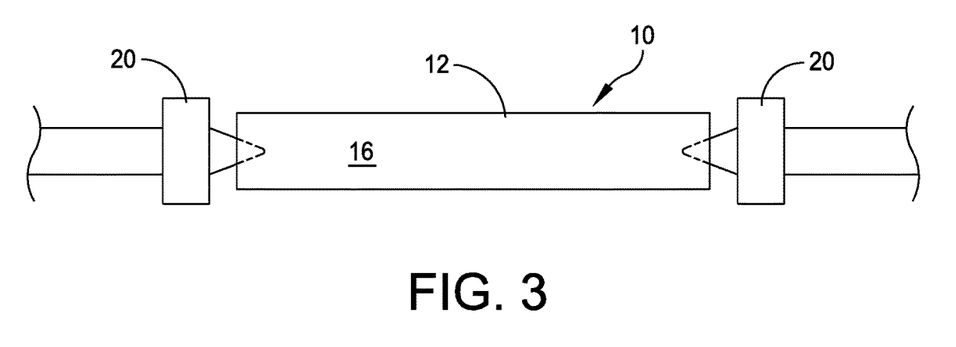
FIG. 3 illustrates a side view of a long bone diaphysis mounted between two live centers.

Turning to the exemplary embodiments shown in the figures, FIGS. 2A-2B provide a flowchart depicting an exemplary method (100) of harvesting periosteum from a human long bone 10 and processing it into individual periosteum fibers. In this embodiment, the method (100) initiates with removing the epiphyses 14 of the long bone 10 and securing the diaphysis 12 of the human long bone 10 between two live centers 20 (e.g., lathe centers) for continuous rotation of the long bone (102), as shown in the schematic of FIG. 3. The method (100) may continue with scraping or removing the periosteum tissue 16 from the rotating long bone 10 until only the cortical bone 18 remains (104), utilizing one or more periosteum harvesting or scraping tools selected from an embodiment of a periosteum harvesting and processing kit 30, as shown in FIG. 4.

Figure 4:
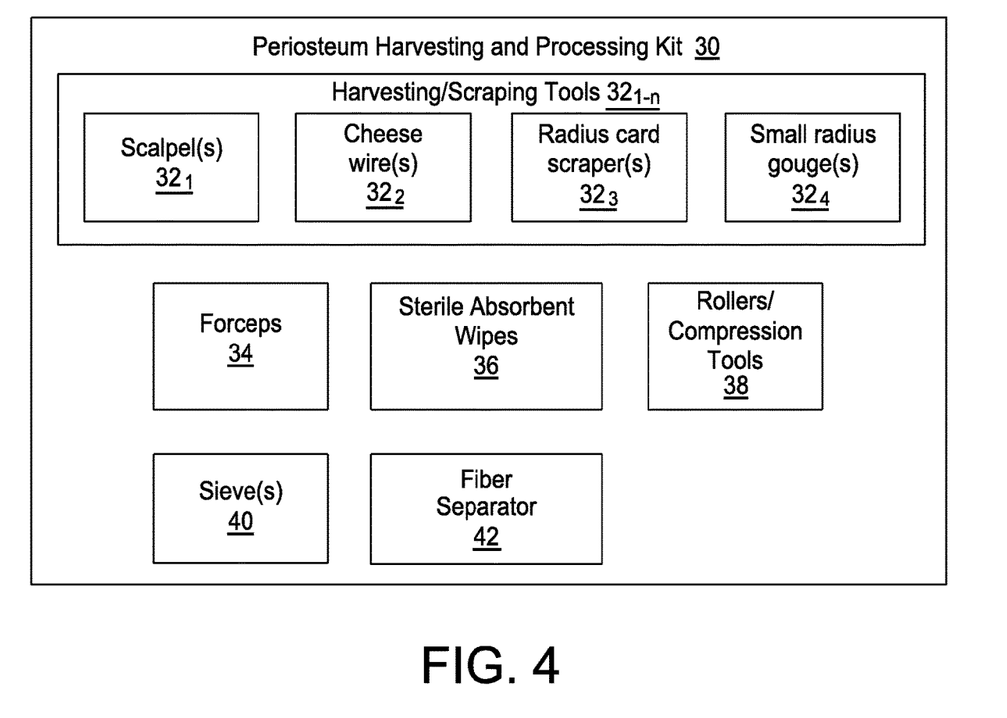
FIG. 4 provides a functional block diagram depicting one embodiment of a periosteum harvesting and processing kit.
Figure 5:
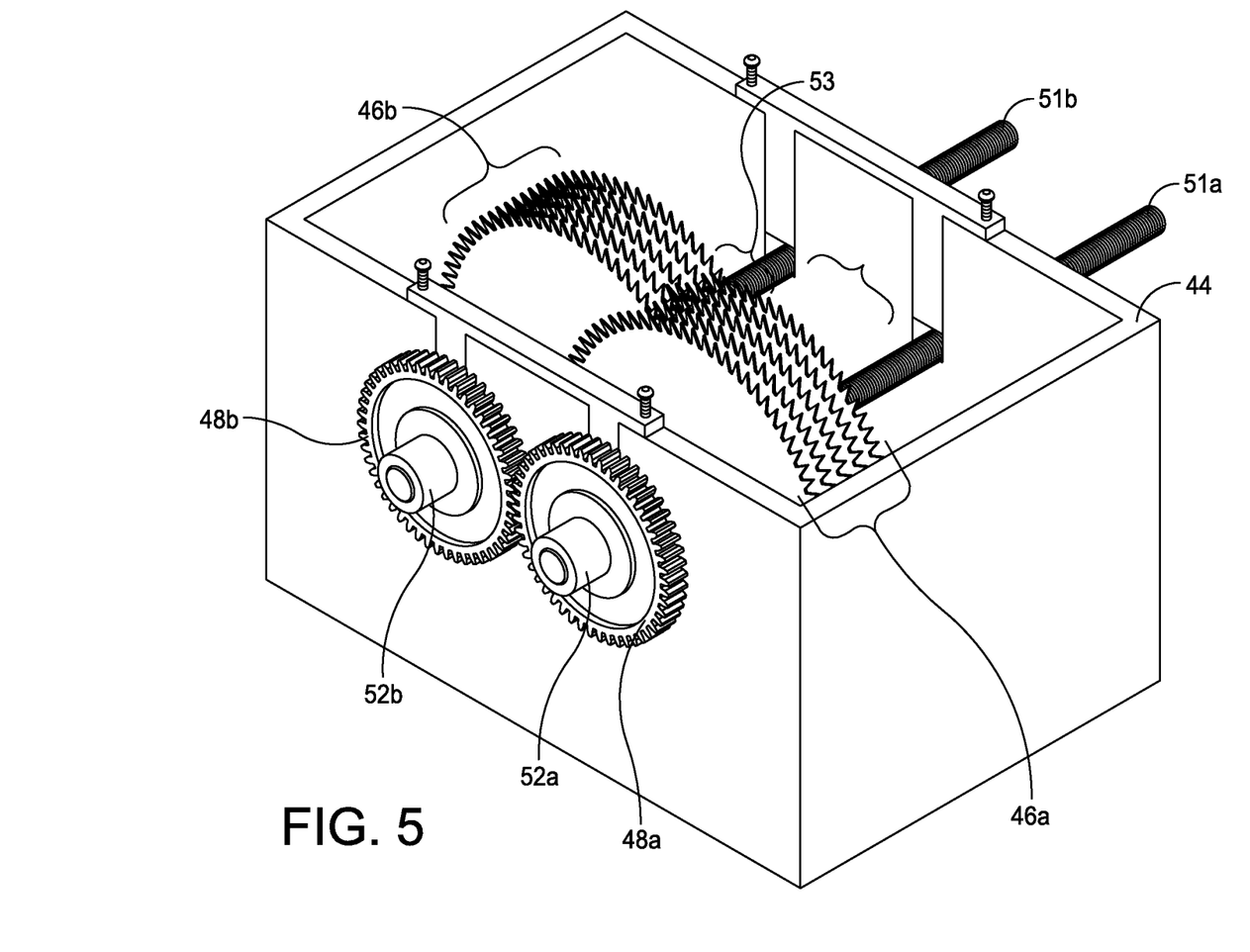
FIGS. 5-9 illustrate respective left-perspective, top, right-perspective, rear-perspective, and front views of one embodiment of a periosteum fiber separator tool.
Figure 6:
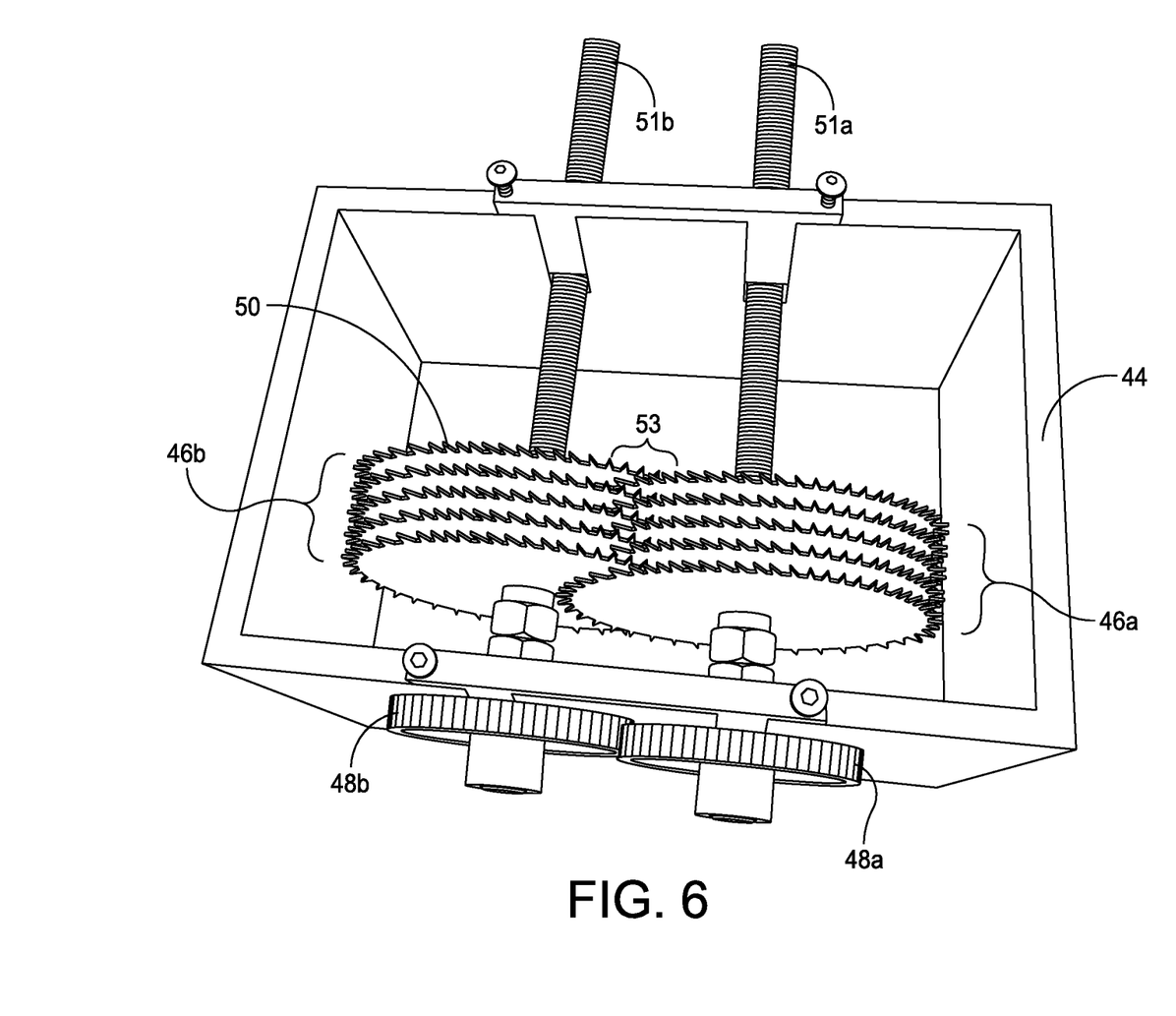
Figure 7:
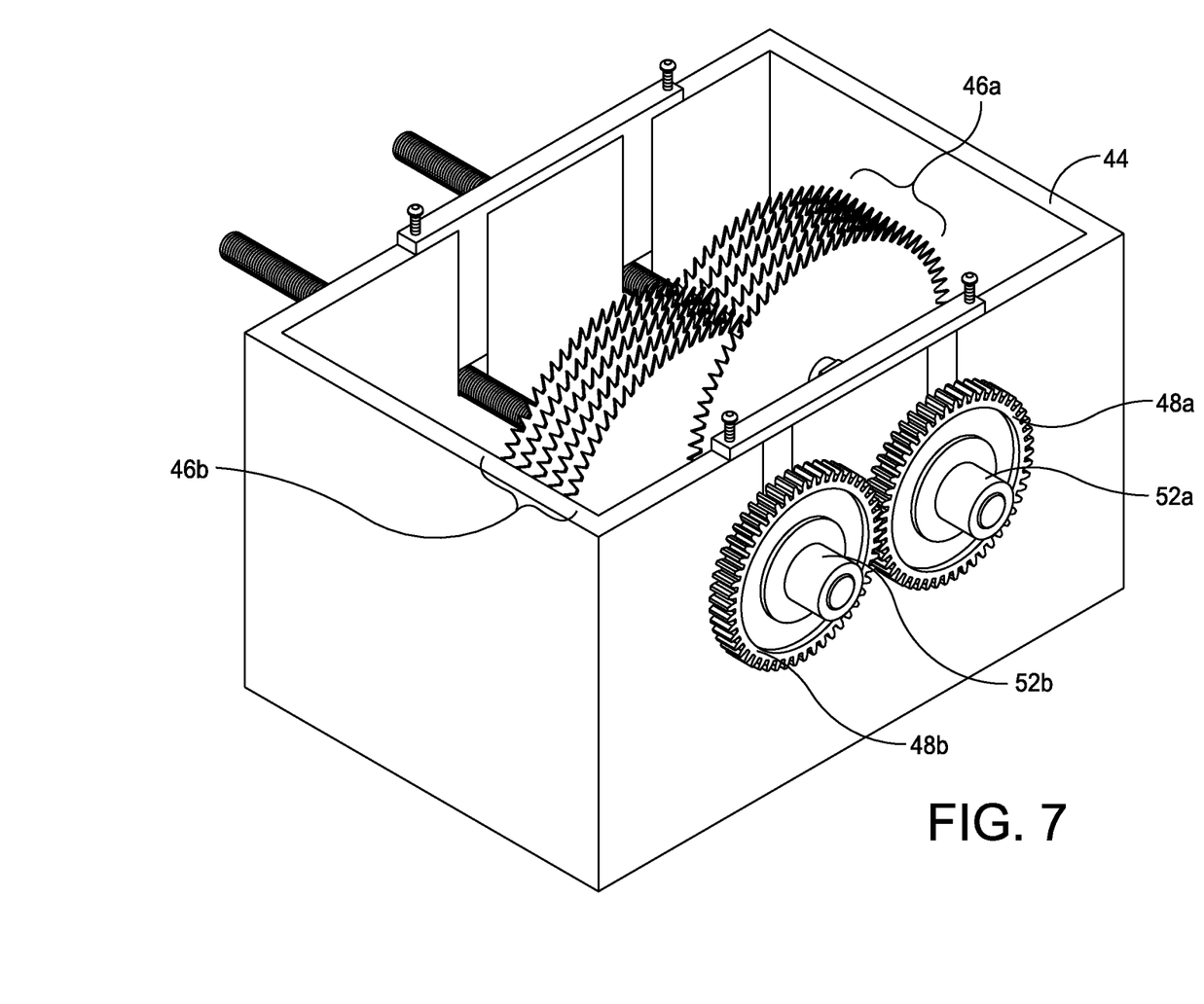

In this regard, FIG. 4 provides a functional block diagram depicting one embodiment of the harvesting and processing kit 30 featuring a plurality of periosteum harvesting or scraping tools 321-$n$ including, for example, one or more scalpels 321, cheese wires 322, radius card scrapers 323, and/or small radius gouges 324. Embodiments of the harvesting and processing kit 30 may also include any appropriate number, variety, and/or type of additional tools necessary to efficiently and rapidly divest the bone 10 of the periosteum tissue 16, as well as tools for further processing of the periosteum 16 including, for instance, one or more forceps 34, sterile absorbent wipes 36, sieves 40, and/or compression tools 38 such as rollers, as discussed in use below.

Returning to FIGS. 2A-2B, and once the periosteum tissue 16 has been scraped from the bone 10, the periosteum tissue 16 undergoes a first wash cycle (106) involving three repetitions of a first wash (108), each time with a 200 ml volume of 6% hydrogen peroxide for five minutes with agitation. After each first wash (108), the periosteum tissue 16 may be isolated using a 125-micron sieve 40 to remove excess hydrogen peroxide (110). After the third repetition of the first hydrogen peroxide wash (108) and the third isolation (110), the periosteum tissue 16 may be dried using pressure applied through one or more of the sterile absorbent wipes 36 (112).

Next, the periosteum tissue 16 may undergo a second wash cycle (114) involving two repetitions of a second wash (116), each time with a 200 ml volume of 70% Isopropyl alcohol for 5 minutes with agitation. After each second wash (116), the periosteum 116 may be isolated or recovered with the 125-micron sieve 40 (118). Following the second repetition of the second wash (116) and the second sieve isolation (118), the periosteum tissue 16 may again be dried using pressure applied through one or more of the sterile absorbent wipes 36 (120).

After the second wash cycle (114), the periosteum tissue 16 undergoes a third wash cycle (122) involving a single third wash (124) with a 200 ml volume of phosphate buffered saline (PBS) for 5 minutes. After this third wash (124), the periosteum tissue 16 is isolated (126) using the 125-micron sieve 40 to remove the excess PBS. The periosteum tissue 16 is then dried using pressure (e.g., manual pressure) applied through one or more of the sterile absorbent wipes 36 (128).

After completing the first, second, and third wash cycles (106, 114, 122), the periosteum tissue 16 may be laid upon a clean sterile absorbent wipe 36 in a manner that results in the tissue having a consistent thickness (130). In one embodiment, the wipe 36 may folded or wrapped around the periosteum tissue 16 (132) before the wipe 36, containing the periosteum tissue 16 therein, is rolled through a space between two adjacent rollers 38 or other compression tools (134), thereby compressing the periosteum/wipe configuration and removing any excess fluids from the periosteum tissue 16. In one embodiment, the periosteum/wipe configuration is rolled at least five times through the rollers 38. After each pass, the rollers may be moved incrementally closer together to incrementally decrease the space between the rollers and provide a resulting incremental increase in periosteum tissue compression (136).

Once the periosteum tissue 16 has been rolled/compressed (134, 136), it may be removed from the sterile absorbent wipe 36 (138) using the sterile forceps 34 before being freeze fractured, or cryofractured (140), utilizing, in one embodiment, the cryofracturing method or a modification of the cryofracturing method disclosed in issued U.S. Pat. No. 9,801,976B2. With a limited volume of crushed dry ice added to a cryofracturing chamber, two-second pulses of cryofracturing may be applied until a desired fiber size of the periosteum tissue 16 is achieved. The crushed dry ice and periosteum fiber mixture are then removed from the cryofracturing chamber and laid on a clean sterile wipe 36 to allow for the dry ice to evaporate (142).

After complete evaporation of the dry ice (142), the clumps of bulk periosteum tissue 16, each formed of a plurality of fused periosteum fibers, may be separated into individual periosteum fibers (144) by processing the bulk tissue through a separation tool or separator that may be included in the periosteum harvesting and processing kit 30 of FIG. 4.

FIGS. 5-9 illustrate left-perspective, top, right-perspective, rear-perspective, and front views of one embodiment of a fiber separator 42, respectively. In this embodiment, the fiber separator 42 may include a housing 44 containing first and second sets of overlapping, circular serrated blades 46a, 46b configured for counterrotation during operation. The first blade set 46a may be operatively coupled with a first gear 48a via a first drive shaft 51a, and the second blade set may be operatively coupled with a second gear 48b via a second drive shaft 51b. The gears 48a, 48b may be enmeshed such that, when at least one of the gears 48a, 48b is rotated, the blades of the respective attached blade sets 46a, 46b rotate in opposite directions. The gears 48a, 48b may take any appropriate size, shape, and/or configuration. As shown, the gear 48a, 48b may include or be attached to manual knobs 52a, 52b to facilitate the rotation of the gears. In other embodiments, the gears 48a, 48b may be attached to other types of knobs or cranks as desired and/or appropriate. In some embodiments, the gears may be operatively coupled with one or more motors or actuators and controlled electronically.

Figure 8:
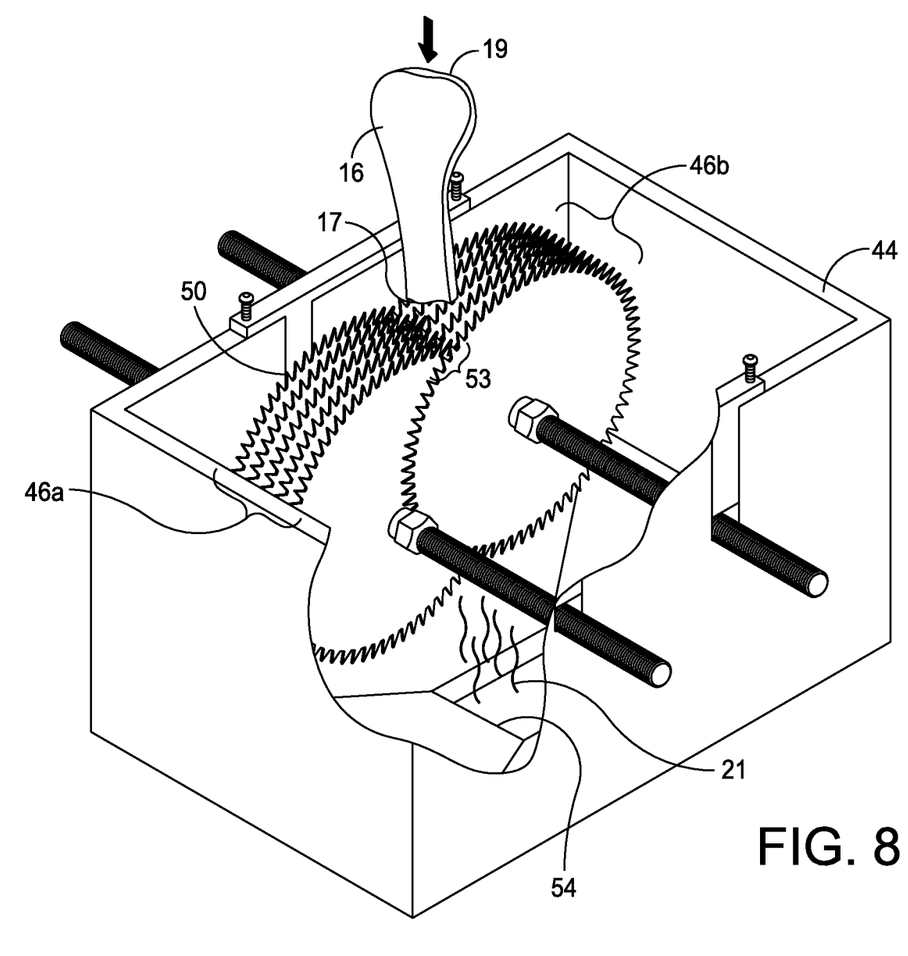
Figure 9:
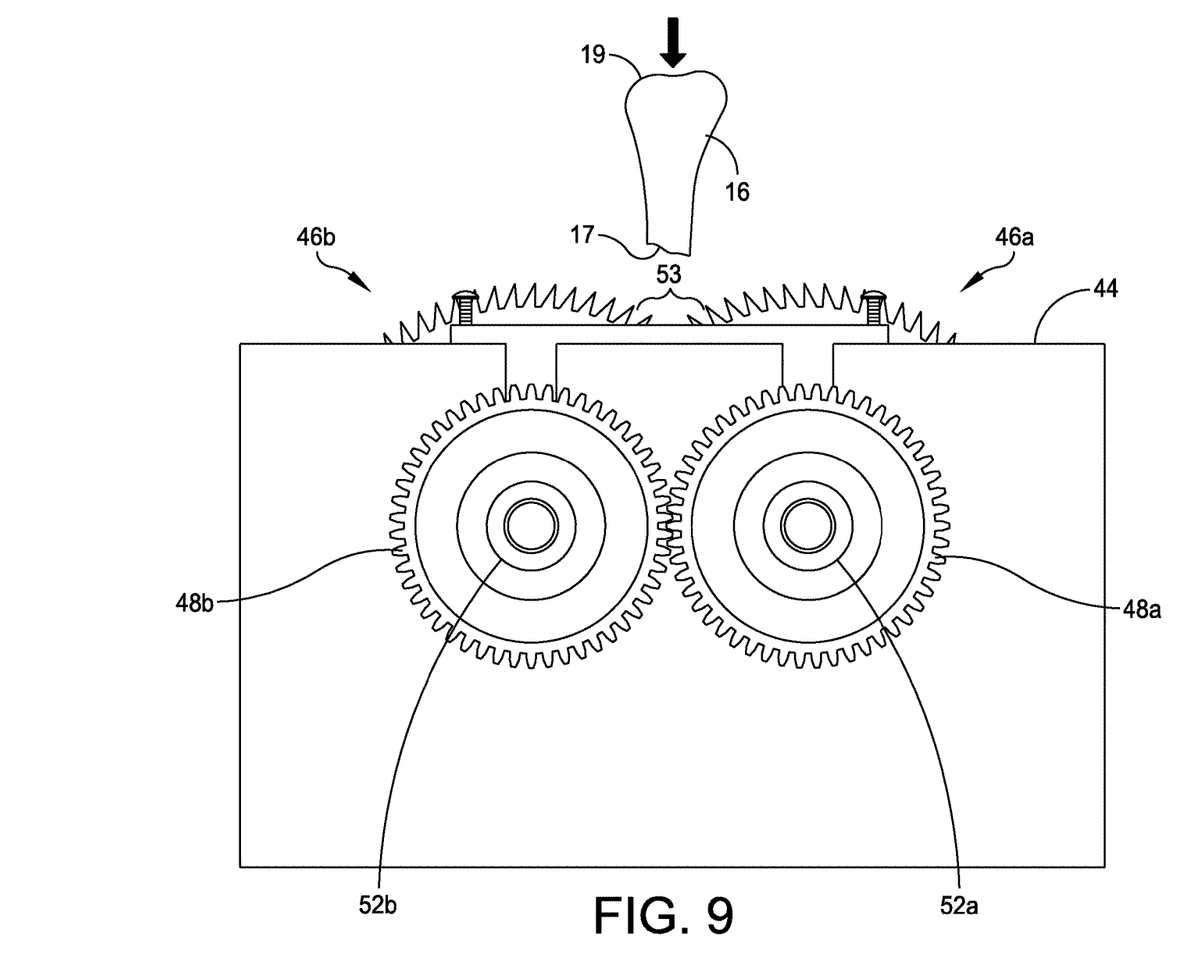

As the bulk periosteum tissue 16 is passed into contact with an overlapping portion 53 of the first and the second blade sets 46a, 46b, the blades 46a, 46b impinge upon the clumps of periosteum tissue 16 such that a number of blade teeth 50 separate the tissue 16 into its individual fibers 21 as the blades 46a, 46b travel from a first end 17 to a second end 19 of the bulk periosteum tissue 16, as shown in FIGS. 8-9. In one embodiment, the bulk tissue 16 may be passed from a top side of the housing 44 and through the counterrotating blade sets 46a, 46b, such that the separated fibers 21 pass out of the housing 44 through an exit aperture 54 formed in a bottom of the housing 44 for collection and use.

Figure 10:
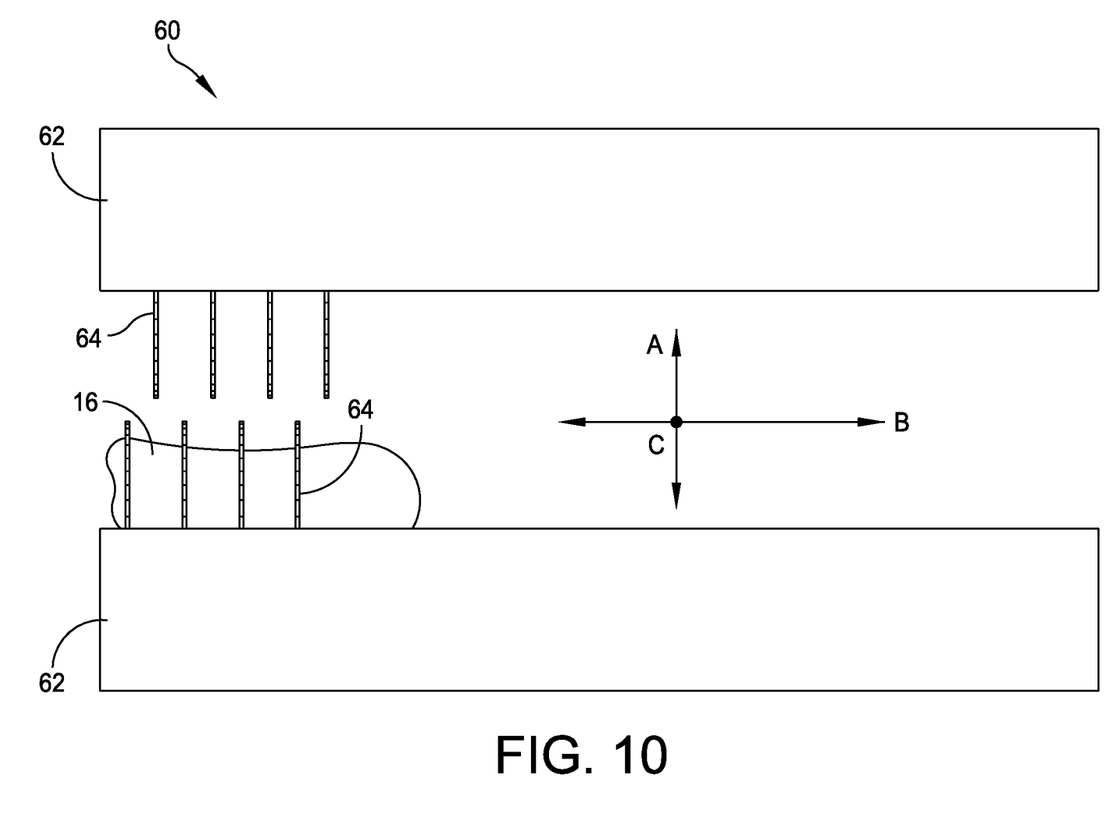
FIG. 10 illustrates a side-plan view of another embodiment of a periosteum fiber separator tool.

In another embodiment shown in FIG. 10, an alternative fiber separator 60 may include first and second opposing blocks 62, each having exposed pin heads 64. The bulk tissue 16 may be placed on the first block 62 and the second block 62 may be placed thereupon along a direction designated by arrow A, such that the pins 64 are used to separate the fibers of the periosteum 16 using a combing motion directed along a longitudinal direction designated by arrow B and/or a lateral direction designated by arrow C, as required for the appropriate surgical application.

Using the systems and associated tools and methods of use described above, a technician or other allograft preparation professional may harvest periosteum tissue 16 from a human long bone 10 and process the tissue into individual periosteum fibers for later use in strengthening surgical allograft products in a manner that is quick, efficient, reliable, and repeatable.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of harvesting and processing bulk periosteum tissue into a plurality of individual, separated periosteum fibers, the method comprising:
   removing, using one or more harvesting tools, a quantity of bulk periosteum tissue from an outer surface of a human long bone;
   first washing the quantity of the bulk periosteum tissue in a volume of hydrogen peroxide;
   second washing the quantity of the bulk periosteum tissue in a volume of isopropyl alcohol;
   third washing the quantity of the bulk periosteum tissue in a volume of phosphate buffered saline (PBS);
   compressing the quantity of the bulk periosteum tissue;
   cryofracturing the quantity of the bulk periosteum tissue with a given number of cryofracturing pulses until the quantity of the bulk periosteum tissue comprises a plurality of fused periosteum fibers having a desired size based on the given number of cryofracturing pulses; and
   using a fiber separator tool to separate the plurality of the fused periosteum fibers from one another into the plurality of individual, separated periosteum fibers, wherein the given number of cryofracturing pulses provides an initial sizing of the fused periosteum prior to the step of using a separating tool to separate the fused periosteum fibers having the desired size based on the given number of cryofracturing pulses.

2. The method of claim 1, wherein:
   the first washing comprises:
      executing a hydrogen peroxide wash of the quantity of the periosteum tissue, the hydrogen peroxide wash comprising a 200 ml volume of a 6% hydrogen peroxide solution for five minutes;
      first isolating the quantity of the bulk periosteum tissue using a sieve;
      repeating the executing the hydrogen peroxide wash and the first isolating the quantity of the bulk periosteum tissue until three cycles of the executing the hydrogen peroxide wash and the first isolating the quantity of the bulk periosteum tissue are completed; and
      first drying the quantity of the bulk periosteum tissue;
   the second washing comprises:
      executing an isopropyl alcohol wash of the quantity of the bulk periosteum tissue, the isopropyl alcohol wash comprising a 200 ml volume of a 70% isopropyl alcohol solution for five minutes;
      second isolating the quantity of the bulk periosteum tissue using the sieve;
      repeating the executing the isopropyl alcohol wash and the second isolating the quantity of the bulk periosteum tissue until two cycles of the executing the isopropyl alcohol wash and the second isolating the quantity of the bulk periosteum tissue are completed; and
      second drying the quantity of the bulk periosteum tissue; and
   the third washing comprises:
      executing a PBS wash of the quantity of the bulk periosteum tissue, the PBS wash comprising a 200 ml volume of the PBS for five minutes;
      third isolating the quantity of the bulk periosteum tissue using the sieve; and
      third drying the quantity of the bulk periosteum tissue.

3. The method of claim 1, wherein the fiber separator tool comprises two sets of counterrotating circular blades, the two sets of the counterrotating circular blades overlapping one another at an overlapping inner portion positioned between the two sets of the counterrotating circular blades, wherein when the quantity of the bulk periosteum tissue contacts the overlapping inner portion of the two sets of the counterrotating circular blades, the two sets of the counterrotating circular blades impinge upon the plurality of the individual periosteum fibers and separate the plurality of the individual periosteum fibers from one another into the plurality of individual, separated periosteum fibers.

4. The method of claim 1, wherein the fiber separator tool comprises first and second opposing blocks, each of the first and the second opposing blocks having an opposing inner surface with a plurality of pins protruding proximally-to-distally therefrom, wherein when the quantity of the bulk periosteum tissue is positioned between the opposing inner surfaces of the first and the second opposing blocks, the plurality of the pins impinge upon the quantity of the individual periosteum fibers and separate the plurality of the individual periosteum fibers from one another.

5. The method of claim 1, wherein the removing the quantity of the bulk periosteum tissue from the outer surface of the human long bone comprises:
 providing the human long bone having a diaphysis extending between two epiphyses, the diaphysis including an outer layer of periosteum tissue;
 removing the epiphyses from the human long bone;
 securing the diaphysis between two rotating live centers; and
 scraping, using the one or more of the harvesting tools selected from a periosteum harvesting and processing kit, the quantity of the bulk periosteum tissue from the diaphysis.

6. The method of claim 5, wherein the periosteum harvesting and processing kit comprises the one or more of the harvesting tools, a forceps, a compression tool, a plurality of sterile absorbent wipes, one or more sieves, and the fiber separator tool.

7. A method for harvesting and processing periosteum tissue into a plurality of individual, separated periosteum fibers, comprising:
 providing a periosteum harvesting and processing kit comprising a plurality of periosteum harvesting tools configured for removing an outer layer of periosteum tissue from a human long bone, at least one sieve, at least one compression tool, and a periosteum fiber separator;
 using at least one of the plurality of the periosteum harvesting tools, removing the periosteum tissue from the human long bone;
 thrice repeating a first wash cycle with a hydrogen peroxide wash;
 first drying the periosteum tissue;
 twice repeating a second wash cycle with an isopropyl alcohol wash cycle;
 second drying the periosteum tissue;
 performing a third wash cycle with a phosphate buffered saline (PBS) wash;
 third drying the periosteum tissue;
 compressing the periosteum tissue using the at least one compression tool;
 cryofracturing by applying a given number of cryofracturing pulses to the periosteum tissue until a plurality of fused periosteum fibers has a desired sized based on the given number of cryofracturing pulses; and
 separating the plurality of the fused periosteum fibers into a plurality of individual periosteum fibers using the periosteum fiber separator so as to provide a controlled process that includes a first step of creating the plurality of fused periosteum with the desired size, and a second step of separating the plurality of fused periosteum into the individual periosteum fibers.

8. The method of claim 7, wherein:
the first wash cycle with the hydrogen peroxide wash comprises:
 first washing the periosteum tissue in a volume of hydrogen peroxide; and
 first isolating the periosteum tissue using the at least one sieve;
the alcohol wash cycle with the second isopropyl alcohol wash comprises:
 second washing the periosteum tissue in a volume of isopropyl alcohol; and
 second isolating the periosteum tissue using the at least one sieve; and
the third cycle with the PBS wash comprises:
 third washing the periosteum tissue in a volume of PBS; and
 third isolating the periosteum tissue using the at least one sieve.

9. The method of claim 7, wherein:
the periosteum fiber separator comprises first and second overlapping and counterrotating blade sets respectively and operatively coupled with first and second enmeshed gears; and
the separating the plurality of the fused periosteum fibers comprises:
 rotating at least one of the first and the second enmeshed gears to rotate the first and the second overlapping and counterrotating blade sets in opposite directions; and
 inserting the plurality of the fused periosteum fibers into an overlapping portion between the first and the second overlapping and counterrotating blade sets, such that the first and the second overlapping and counterrotating blade sets impinge upon the plurality the fused periosteum fibers and cause the fused periosteum fibers to separate into the plurality of the individual periosteum fibers as the first and the second overlapping and counterrotating blade sets travel from a first end to a second end of the plurality of the fused periosteum fibers.

10. The method of claim 7, wherein:
the periosteum fiber separator comprises first and second opposing blocks, each of the first and the second opposing blocks having an opposing inner surface with a plurality of pins protruding outward therefrom;
the separating the plurality of the fused periosteum fibers comprises:
 positioning the plurality of the fused periosteum fibers between the opposing inner surfaces of the first and the second opposing blocks; and
 impinging the plurality of the pins upon the plurality of the fused periosteum fibers such that the plurality of the fused periosteum fibers fracture into the plurality of the individual periosteum fibers.

11. The method of claim 7, wherein the removing the outer layer of the periosteum tissue from the human long bone comprises:
 securing a diaphysis of the human long bone between two rotating live centers;
 scraping, using the at least one of the plurality of the periosteum harvesting tools selected from the periosteum harvesting and processing kit, the outer layer of the periosteum tissue from the diaphysis.

* * * * *